United States Patent [19]

Kapp

[11] 4,013,790

[45] Mar. 22, 1977

[54] PHOSPHINE-DEVELOPING PESTICIDE AND PROCESS FOR PRODUCTION THEREOF

[75] Inventor: Wolfgang Kapp, Offenbach (Main), Germany

[73] Assignee: Deutsche Gesellschaft fur Schadlingbekampfung mbH, Frankfurt am Main, Germany

[22] Filed: Sept. 10, 1975

[21] Appl. No.: 611,848

[30] Foreign Application Priority Data

Sept. 11, 1974 Germany .......................... 2443333

[52] U.S. Cl. ............................... 424/128; 424/78; 424/286
[51] Int. Cl.² .................................... A01N 11/00
[58] Field of Search ................................... 424/128

[56] References Cited

UNITED STATES PATENTS

| 3,132,067 | 5/1964 | Rauscher et al. | 424/128 X |
| 3,917,823 | 11/1975 | Kapp | 424/128 |

OTHER PUBLICATIONS

Chemical Abstracts 75:77562r (1971).

*Primary Examiner*—Leonard Schenkman
*Attorney, Agent, or Firm*—Gordon W. Hueschen

[57] ABSTRACT

The present invention relates to a phosphine-developing pesticide which comprises at least one phosphide selected from the group consisting of magnesium phosphide and aluminium phosphide, a thermally decomposable material and polyethylene oxide having a molecular weight of between 4000 and 12000 and to a process for producing the same.

17 Claims, No Drawings

PHOSPHINE-DEVELOPING PESTICIDE AND PROCESS FOR PRODUCTION THEREOF

The present invention relates to phosphine-developing pesticides.

More particularly, the present invention relates to phosphine-developing pesticides with a content of magnesium phosphide and/or aluminium phosphide, a thermally decomposable material and at least one other additive and to a process for the production of such a pesticide.

When pest control is effected with phosphine, the latter is usually released from metal phosphides by hydrolysis. Suitable metal phosphides, such as calcium phosphide ($Ca_3P_2$), magnesium phosphide ($Mg_3P_2$) of aluminium phosphide (AlP) react even at room temperature with the moisture from the air and thereby release gaseous phosphine. Since under certain circumstances the phosphine released from metal phosphides can ignite spontaneously in the air, special measures are necessary to prevent reliably such spontaneous ignition. In addition, attempts are made to adapt the speed of development of the phosphine to the special conditions in the control of pests, so as to eliminate risk to the personnel as a result of premature phosphine development.

It is known to add various inorganic and/or organic substances to the metal phosphides in order to influence the speed of formation of the phosphine and/or the spontaneous inflammability of the phosphine in the desired manner.

In accordance with German Specification No. 923,006 the spontaneous inflammability of phosphides of alkalis, alkaline earths or earth metals such as the rare earth metals and of phosphine which is developed therefrom, in particular by hydrolysis in humid air, is suppressed by substances, which thermally are easily decomposable and which preferably split off carbon dioxide, e.g. sodium bicarbonate, ammonium carbamate or salt of hartshorn (ammonium carbonate), being mixed with these metal phosphides. However, the speed of formation of the phosphine is influenced only slightly or not at all by these additives.

In accordance with the German Auslegeschrift No. 1,023,265 the phosphides of the alkalis, alkaline earths and earth metals such as the rare earth metals are mixed with highly volatile, organic fluids, which produce a cooling effect due to evaporation, in order to suppress the spontaneous inflammability and to regulate the speed of formation of the phosphines which develop from the former substances.

During vaporization of these fluids which produce a cooling effect due to evaporation, atmospheric humidity is of necessity also condensed, which often accelerates the phosphine development undesirably. Moreover, during transport and storage, a premature vaporization of the highly volatile organic fluid must be reckoned with.

In the German Auslegeschrift No. 1,155,631, highly volatile solid organic substances are mentioned, which are mixed with alkali phosphides, alkaline earth phosphides or earth metal phosphides such as the rare earth metal phosphides in order to influence the speed of formation of the phosphine. By means of these additives the speed of formation of the phosphine is to be regulated and, in addition, its spontaneous inflammability is to be suppressed, whilst in some cases the encasing of pieces of metal phosphide with water-soluble or water-pervious jackets is simply to lead to a retardation in the ignition of the phosphine/air mixture.

In accordance with the German Specification No. 1,122,762, the cooperation of metal phosphide, whose individual particles or small particle groups are encased by a thick layer of water-repellent organic solid substance, with a thermally decomposable substance yields a moisture-protected metal phosphide for the control of pests.

In practice it has become evident that water-repellent encasing substances around the metal phosphide inhibit the penetration of the metal phosphide by water, whereby the speed of formation of the phosphine is retarded to the desired extent. However, in many cases, water-repellent encasing substances of this kind result in a reduction in the utilisation of the metal phosphide, since the encased metal phosphide is not completely converted during the gradual hydrolysis effected as a result of atmospheric humidity. Thus, in the case of a pesticide comprising 80% by weight of aluminium phosphide, 3% by weight of paraffin and the remainder inert material, after 120 hours of releasing gas there was still 5.2% of the aluminium phosphide originally present detected in the residues. These residual contents of non-converted metal phosphide present special difficulties with respect to the elimination of the pesticide residues.

The elimination of these residues has hitherto basically been effected by burning or burying. However, it has become apparent that these elimination processes are not without drawbacks; for example, the burying of residues has been forbidden in some countries on grounds of the accompanying dangers. In accordance with a more recent proposal, the residues produced subsequent to pest control are eliminated by introduction into water in the liquid phase. In this case the water-repellent, organic constituent of the pesticide retards the elimination of the residues.

Accordingly, the present invention seeks to provide a phosphine-releasing pesticide composed of metal phosphides, which pesticide is protected against spontaneous ignition, and which, when used, initially releases the phosphine in a retarded manner and yields residues which can be eliminated using water in the liquid phase.

In accordance with the invention this aim may be solved in that a solid organic substance is added to a mixture, known per se, of magnesium phosphide and/or aluminium phosphide and thermally decomposable material, which substance delays water in the vapour phase (atmospheric humidity) from gaining access to the metal phosphide, but which on the other hand rapidly dissolves in water in the liquid phase and with which rapid elimination of the residues in the water is ensured. Surprisingly, it has become evident that the use of a substance which regulates the phosphine development also yields a pesticide which is adequately protected against spontaneous ignition, even when the pesticide comes in contact with water in the liquid phase, contrary to specified utilisation.

The phosphine-developing pesticide according to the present invention containing magnesium phosphide and/or aluminium phosphide, a thermally decomposable substance and at least one other additive, is characterised in that the other additive which the pesticide contains is polyethylene oxide having a molecular weight of between 4000 and 12000. The pesticide according to the present invention preferably contains polyethylene oxide with a molecular weight of 5000 to 6000.

As used herein the term "polyethylene oxide" signifies polymeric organic compounds having the following general formula:

$$HOCH_2-(CH_2-O-CH_2)_n-CH_2OH.$$

Compounds having n values of between 90 and 270 are very suitable in accordance with the present invention, because these compounds have the consistency of hard wax and can readily be ground to a fine powder, and have solidification points ranging from 50° to 62° C. Polyethylene oxides having a molecular weight which is clearly less than 4000, i.e. compounds according to the above formula having values for n which are considerably less than 90, are less suitable for the production of the pesticides according to the present invention, since such polyethylene oxides soften even at those temperatures which may arise during transport and storage; furthermore, low-molecular polyethylene oxides of this type cannot readily be ground to powders having small-size granules, such as are desirable in the production of the pesticides according to the present invention. Polyethylene oxides having molecular weights which are clearly in excess of 12000, i.e. compounds having the above general formula with values for n which are considerably more than 270, are less suitable for the production of the pesticides according to the present invention because, under the simple processing conditions which are aimed at, these high-molecular polyethylene oxides do not have the required creeping capacity to encase all the metal phosphide particles with an even layer of polyethylene oxide which is dense enough to delay atmospheric humidity gaining access to the metal phosphide. In the production of the pesticides according to the present invention those polyethylene oxides have proved to be particularly suitable whose molecular weight is between 5000 and 6000; in accordance with the above general formula these are compounds having values for n ranging from approximately 110 to 135. These polyethylene oxides have solidification points ranging from approximately 55° to 62° C and, under the desired simple processing conditions, form a particularly extensive, even, protective casing around the individual particles of metal phosphide.

Since the above-mentioned polyethylene oxides can be combined with metal phosphides which are sensitive to hydrolysis, the polyethylene oxides are to be substantially anhydrous; in practice, it has become evident that a moisture content of up to 1% by weight can be tolerated. Those polyethylene oxides which are in the form of a finely ground powder are particularly suitable for the production of the pesticides of the present invention, since such powdery polyethylene oxides are easy to mix with the metal phosphide and the thermally decomposable material. Polyethylene oxide powder having an average granular size of less than 100μ is extremely suitable, polyethylene oxide powder having average granular sizes of between 5 and 75μ being particularly preferred.

In the pesticide according to the present invention the polyethylene oxide additive serves to adapt the speed of development of the phosphine to the conditions which are aimed at in practice. When controlling pests with phosphine-developing pesticides, it is desired that, subsequent to its removal from the packing, which prevents the penetration of moisture, the agent contacts the atmospheric humidity and releases the phosphine slowly in order to avoid endangering the workers during distribution of the pesticide in the area which is to be treated or during the introduction thereof into the material which is to be treated. After the initial, slow development of phosphine, the phosphine is to be released at an average, even speed as the treatment continues. It has become evident that a pesticide composed of magnesium phosphide and/or aluminium phosphide mixed with a thermally decomposable material, to which 2 to 14% by weight of the above-mentioned polyethylene oxide has been added, meet these requirements particularly well. In practice, it has become apparent that at least 2% by weight of polyethylene oxide is required to coat all the metal phosphide particles with an even layer of polyethylene oxide. Although there are no objections against using more than 14% by weight of polyethylene oxide, there are no further advantages to be gained thereby and therefore this is not implemented on economical grounds. A polyethylene oxide content of 3 to 8% by weight is particularly preferred within the limits of the present invention, since it has become apparent that, under the production conditions provided in accordance with the present invention, a particularly even, substantially dense coating of polyethylene oxide around the individual metal phosphide particles is thereby achieved.

Table I following shows that a clearly retarded phosphine development occurs in the pesticides according to the present invention having an addition of at least 4% by weight of polyethylene oxide, as compared with a mixture of non-encased aluminium phosphide and ammonium carbamate.

In order to determine the speed of the phosphine development of pesticides according to the present invention and of comparative preparations, 12 pellets of the composition given in column 1 were in each case placed in a steel chamber with an inner volume of 2 m³, which chamber could be sealed tight, and a temperature of 19° to 20° C was maintained. A constant atmospheric humidity of approximately 60% relative humidity was set in the interior of the steel chamber. After the prescribed times, samples of gas were removed from the interior of the steel chamber through an appropriate opening, and the phosphine content of these gas samples was determined with "Dräger tubes".

Table I

Initial phosphine development under the action of atmospheric humidity on preparations according to the present invention and comparative preparations composed of aluminium phosphide (A1P), ammonium carbamate (Carb) and polyethylene oxide (PEO)

| Sample | | | Phosphine content of the gas sample (ppm) after | | | | | |
|---|---|---|---|---|---|---|---|---|
| | | | 15 mins. | 30 mins. | 60 mins. | 120 mins. | 180 mins. | 240 mins. |
| 70 A1P | 26 Carb | 4 PEO | 6 | 18 | 35 | 95 | 145 | 200 |
| 66 A1P | 26 Carb | 8 PEO | 7 | 13 | 26 | 60 | 115 | 150 |

Table I-continued

Initial phosphine development under the action of atmospheric humidity on preparations according to the present invention and comparative preparations composed of aluminium phosphide (AlP), ammonium carbamate (Carb) and polyethylene oxide (PEO)

| Sample | | | Phosphine content of the gas sample (ppm) after | | | | | |
|---|---|---|---|---|---|---|---|---|
| | | | 15 mins. | 30 mins. | 60 mins. | 120 mins. | 180 mins. | 240 mins. |
| 62 AlP | 26 Carb | 12 PEO | 5 | 11 | 25 | 55 | 90 | 140 |
| 70 AlP | 30 Carb | | 12 | 23 | 50 | 110 | 170 | 230 |

Thus it can be seen from the results of the tests that under the same conditions and within the test period the pesticides according to the present invention containing polyethylene oxide were able to develop less phosphine than mixtures of metal phosphide with carbamate without the addition of polyethylene oxide. The only explanation for this finding is that in the pesticides according to the present invention the polyethylene oxide forms a dense coating around the individual metal phosphide particles, which inhibits the atmospheric humidity from gaining access to the metal phosphide, and this leads to a retardation in the release of phosphine.

An important constituent of the pesticide according to the present invention is the thermally decomposable material. Suitable materials decompose to a perceptible extent even at temperatures of less than 60° and in the course thereof develop inert gaseous decomposition products. In a manner known per se, ammonium bicarbonate, sodium bicarbonate, salt of hartshorn (ammonium carbonate) and ammonium carbamate are extremely suitable thermally decomposable substances, ammonium carbamate being particularly preferred.

It has become apparent that the conversion of the metal phosphine contained in the pesticides according to the present invention can be further completed if, in addition to the above-mentioned constituents, the agent also contains dry sodium oxide, sodium hydroxide and/or potassium hydroxide. For example, it has been shown that even under optimum conditions for the use of pesticides containing aluminium phosphide, wherein the aluminium phosphide has an encasing layer of water-repellent, solid, organic substance, the residues which are produced subsequent to the pest control still contain approximately 5 to 8% of the aluminium phosphide originally present. The addition of sodium oxide, sodium hydroxide and/or potassium hydroxide can cause the residual content of non-converted metal phosphide to drop to less than 2% of the phosphide originally present. Such a reduction in the residual content of non-converted metal phosphide, in cooperation with an encasing substance which dissolves rapidly in water in the liquid phase, yields a phosphine-developing pesticide, whose residues can be eliminated particularly rapidly and easily by means of water in the liquid phase.

In the development of the present invention it has been found that a phosphine-developing pesticide of the following composition is particularly suitable:
  10 to 30% by weight of ammonium carbamate
  2 to 14% by weight of polyethylene oxide
  0 to 25% by weight of sodium oxide, sodium hydroxide and/or potassium hydroxide
  Remainder: Magnesium phosphide and/or aluminium phosphide with random quantities of inert material.

A mixture of this composition may, without the addition of pressing adjuvants, be pressed to form pressed articles. The pesticide according to the present invention is preferably in the form of pressed articles, such as tablets or pellets.

For the production of the pesticides according to the present invention, atmospheric humidity is excluded during mixing of the above-mentioned, finely-dispersed constituents, and the mixture is then pressed to form pressed bodies. Mixing is effected in known devices. Under the production conditions provided in accordance with the present invention, the polyethylene oxide which is added forms a particularly even, dense coating around the individual metal phosphide particles when powdery polyethylene oxide is used having granular sizes of less than $100\mu$, particularly with granular sizes ranging from 5 to $75\mu$.

The present invention will now be further illustrated by way of the following Examples without, however, limiting it thereto.

EXAMPLE 1

Under exclusion of atmospheric humidity, 57 parts by weight of powdery, technical aluminium phosphide (average granular size: approximately $3\mu$) with a production-stipulated amount of 10 to 20% by weight of inert constituents (basically aluminium oxide) and 5 parts by weight of powdery polyethylene oxide (average molecular weight: 5000 to 6000; average granular size: approximately $50\mu$) were mixed together at approximately 65° C. After cooling, a pourable powder of phosphide particles, coated with a protective covering of polyethylene oxide, was obtained. 15 parts by weight of dry powdery sodium oxide (granular size: approximately $180\mu$) and 23 parts by weight of ammonium carbamate were added thereto and all the constituents were then mixed thoroughly. The homogeneous mixture which was obtained was then pressed to form tablets approximately 7 mm high and with a diameter of approximately 9 mm.

EXAMPLE 2

70 parts by weight of technical aluminium phosphide (average granular size: approximately $3\mu$), 4 parts by weight of powdery polyethylene oxide (average molecular weight: ranging from 5000 to 6000; average particle size: approximately $60\mu$) and 26 parts by weight of ammonium carbamate were mixed thoroughly for 60 minutes in the same manner as given for Example 1, under exclusion of atmospheric humidity. The mixture obtained was then pressed to form spherical pellets with a diameter of 12 mm.

EXAMPLE 3

65 Parts by weight of powdery magnesium phosphide (granular size: approximately 5 to $50\mu$) with a production-stipulated quantity of approximately 10% inert constituents (basically magnesium oxide), 10 parts by weight of powdery polyethylene oxide (average molecular weight: approximately 12000, average granular size: approximately 10μ) and 25 parts by weight of ammonium carbamate were mixed thoroughly for 40 minutes, in the manner given for Example 1 under exclusion of atmospheric humidity. The mixture obtained was pressed in a tablet press to form tablets.

Tests for the elimination of the residues obtained after the release of gas were carried out on pesticides according to the present invention and on comparative preparations. To enable the release of gas the pressed articles were exposed to a relative atmospheric humidity of 60% for 120 hours in a climatic test chamber at 20° C. The residue was then placed in water and tested.

The results of the tests are shown in Table II following.

The second column of Table II shows that the residues containing the water-soluble PEO of the present invention sink very rapidly whilst the residues containing the hard paraffin or aluminium stearate are not moistened within the observation period of 4 hours, and float on the surface.

Even the residues of pressed articles containing AlP and carbamate sink considerably more slowly.

Table II

Elimination of the pesticide residues, produced after release of gas for 120 hours, in fluid water

| Pesticide | Length of time taken for entire residue to sink in 200 ml of water |
| --- | --- |
| 58 AlP/23 Carb/4 PEO*/15 Na$_2$O | <30 secs. |
| 63 AlP/23 Carb/4 PEO/10 Na$_2$O | <30 secs. |
| 70 AlP/26 Carb/4 PEO | <30 secs. |
| 66 AlP/26 Carb/8 PEO | <30 secs. |
| 62 AlP/26 Carb/12 PEO | <30 secs. |
| 70 Mg$_3$P$_2$/26 Carb/4 PEO | <30 secs. |
| 66 Mg$_3$P$_2$/26 Carb/8 PEO | <30 secs. |
| 62 Mg$_3$P$_2$/26 Carb/12 PEO | <30 secs. |
| 70 AlP/26 Carb/4 HP** | No moistening within 4 hrs. |
| 70 AlP/26 Carb/4 Al-St*** | No moistening within 4 hrs. |

*PEO represents polyethylene oxide
**HP represents hard paraffin
***Al-St represents aluminium stearate The results of the tests show that adding polyethylene oxide to the mixture, known per se, of magnesium phosphide and/or aluminium phosphide and ammonium carbamate yields a pesticide whose residues, produced subsequent to pest control, can rapidly be eliminated in water and in the liquid phase.

EXAMPLE 4

Sixty-six parts by weight of technical aluminum phosphide (granular size: 3 to 150μ) and seven parts by weight powdery polyethylene oxide (average molecular weight: 5000 to 6000), having a granular size of between 80 and 120μ, were mixed at 65° to 70° C.

After cooling, 27 parts by weight of sodium bicarbonate having a granular size between 40 and 200μ were added to the resultant powder while in a non-caking condition. After subsequent mixture to homogeneity, tablets of the size described in Example 1 were pressed.

The temperature stability of the product according to the present invention is extremely good; not only transient heat but also heat of longer duration not only fail to cause damage in dense packing at elevated storage temperatures, but also contribute to an improvement both in the keeping qualities and in the protective coating of the pressed bodies.

As already stated, suitable decomposition products in the sense of the application are chemical compounds having the property to release gases by thermal dissociation. In the temperature range between 20° and 65° C, a decomposition vapor pressure of at least 50 Torr is to be achieved. Preferred substances are those releasing ignition-retarding gases such as carbon dioxide. Otherwise, this ingredient is not of a critical nature, and many such materials are known in the art. Representative examples of such thermally-decomposable materials are: ammonium carbamate, ammonium carbonate (salt of hartshorn), sodium bicarbonate, and ammonium cyanide.

Various modifications in the compounds, compositions, and method of the invention will be apparent to one skilled in the art and may be made without departing from the spirit or scope thereof, and it is therefore to be understood that the invention is to be limited only by the scope of the appended claims.

I claim:
1. A phosphine-developing pesticide which comprises (1) a phosphide selected from the group consisting of magnesium phosphide and aluminum phosphide, (2) a thermally decomposable material, comprising a chemical compound which releases a gas in the temperature range between 20° and 65° C to give a vapor pressure of at least 50 Torr., in amount of about 10 to 30 percent by weight, and (3) about 2 to 14 percent by weight of ethylene oxide polymer having a molecular weight of between 4000 and 12000.

2. A pesticide as claimed in claim 1, in which the ethylene oxide polymer has a molecular weight ranging from 5000 to 6000.

3. A pesticide as claimed in claim 1, in which 3 to 8% by weight of the ethylene oxide polymer is present.

4. A pesticide as claimed in claim 1 in which the metal phosphide is present in the form of individual particles and the individual particles have a dense coating of ethylene oxide polymer, which delays atmospheric humidity from gaining access to the metal phosphide.

5. A pesticide as claimed in claim 1 in which the thermally decomposable material is ammonium carbamate.

6. A pesticide as claimed in claim 5, which comprises 10 to 30% by weight of ammonium carbamate, 2 to 14% by weight of ethylene oxide polymer, 0 to 25% by weight of at least one compound selected from the group consisting of sodium oxide, sodium hydroxide and potassium hydroxide and the remainder at least one phosphide selected from the group consisting of magnesium phosphide and aluminum phosphide with random quantities of inert material.

7. A pesticide as claimed in claim 1, which also comprises at least one compound selected from the group consisting of dry sodium oxide, sodium hydroxide and potassium hydroxide.

8. A pesticide as claimed in claim 1 which is present in the form of pressed bodies.

9. A pesticide as claimed in claim 8, in which the pressed bodies are in the form of tablets or pellets.

10. A pesticide of claim 1, wherein the decomposable material is one which releases an ignition-retarding gas.

11. A process for producing a phosphine-developing pesticide which comprises mixing together (1) at least one phosphide selected from the group consisting of magnesium phosphide and aluminum phosphide, (2) a thermally decomposable material, comprising a chemical compound which releases a gas in the temperature range between 20° and 65° C to give a vapor pressure of at least 50 Torr., in amount of about 10 to 30 percent by weight, and (3) about 2 to 14 percent by weight of ethylene oxide polymer having a molecular weight of between 4000 and 12000, and subsequently pressing the mixture to form pressed bodies.

12. A process as claimed in claim 11, in which at least one compound selected from the group consisting of sodium oxide, sodium hydroxide and potassium hydroxide is also mixed together with at least one phosphide selected from the group consisting of magnesium phosphide and aluminium phosphide, the thermally decomposable material, and the ethylene oxide polymer having a molecular weight of between 4000 and 12000.

13. A process as claimed in claim 12, in which each component of the mixture is present in a finely-dispersed form.

14. A process as claimed in claim 11, in which powdery ethylene oxide polymer is used having granular sizes of less than $100\mu$.

15. A process as claimed in claim 14, in which the powdery ethylene oxide polymer has granular sizes of between 5 and $75\mu$.

16. A process as claimed in claim 11, in which the thermally decomposable material is ammonium carbamate.

17. A process as claimed in claim 11, in which the pressed bodies are in form of tablets or pellets.

* * * * *

UNITED STATES PATENT OFFICE
CERTIFICATE OF CORRECTION

Patent No. 4,013,790      Dated March 22, 1977

Inventor(s) Wolfgang Kapp

It is certified that error appears in the above-identified patent and that said Letters Patent are hereby corrected as shown below:

Col. 1, Line 16: change "($Mg_3P_2$) of" to read ---($Mg_3P_2$) or---

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*